United States Patent
Ferree

(10) Patent No.: US 6,843,790 B2
(45) Date of Patent: Jan. 18, 2005

(54) ANATOMIC POSTERIOR LUMBAR PLATE

(76) Inventor: Bret A. Ferree, 1238 Cliff Laine Dr., Cincinnati, OH (US) 45208

(*) Notice: Subject to any disclaimer, the term of this patent is extended or adjusted under 35 U.S.C. 154(b) by 0 days.

(21) Appl. No.: 10/108,015

(22) Filed: Mar. 27, 2002

(65) Prior Publication Data

US 2002/0161367 A1 Oct. 31, 2002

Related U.S. Application Data

(60) Provisional application No. 60/279,157, filed on Mar. 27, 2001.

(51) Int. Cl.[7] .............................................. A61B 17/80
(52) U.S. Cl. .......................................... 606/61; 606/69
(58) Field of Search ..................... 606/71, 61

(56) References Cited

U.S. PATENT DOCUMENTS

| 4,611,581 A | | 9/1986 | Steffee | |
|---|---|---|---|---|
| 4,790,297 A | * | 12/1988 | Luque | 606/61 |
| 5,147,361 A | | 9/1992 | Ojima et al. | |
| 5,359,824 A | * | 11/1994 | Koberstein | 411/148 |
| 5,423,826 A | * | 6/1995 | Coates et al. | 606/96 |
| 5,486,176 A | * | 1/1996 | Hildebrand et al. | 606/61 |
| 5,527,312 A | * | 6/1996 | Ray | 606/61 |
| 5,584,887 A | * | 12/1996 | Kambin | 606/61 |
| 5,647,872 A | | 7/1997 | Gilbert et al. | |
| 5,735,850 A | | 4/1998 | Baumgartner | |
| 6,235,034 B1 | * | 5/2001 | Bray | 606/61 |
| 6,306,136 B1 | | 10/2001 | Baccelli | |
| 6,336,927 B2 | | 1/2002 | Rogozinski | |
| 2002/0087159 A1 | * | 7/2002 | Thomas | 606/61 |

FOREIGN PATENT DOCUMENTS

| EP | 0506420 A1 | 9/1992 |
|---|---|---|
| FR | 2758971 A | 8/1998 |
| FR | 2790941 A | 9/2000 |
| WO | WO 9841160 A | 9/1998 |

* cited by examiner

*Primary Examiner*—Kevin Shaver
*Assistant Examiner*—Candice C. Stokes
(74) *Attorney, Agent, or Firm*—Jerrold J. Litzinger

(57) ABSTRACT

An anatomic posterior lumbar system comprising of a thin plate and fasteners for securing the plate to vertebra or other osseous material. The plate is preferably a thin rectangular structure having an opening running lengthwise in its central portion. At least one pedicle screw having a hollow threaded interior is fastened to a vertebra, and the plate located on the screw using the opening. A washer spans the width of the plate, and accommodates an inner screw, which is threaded into the pedicle screw, and captures the head of the inner screw. Miscellaneous shapes of plates are also disclosed which are fitted to specific portions of the spine.

18 Claims, 17 Drawing Sheets

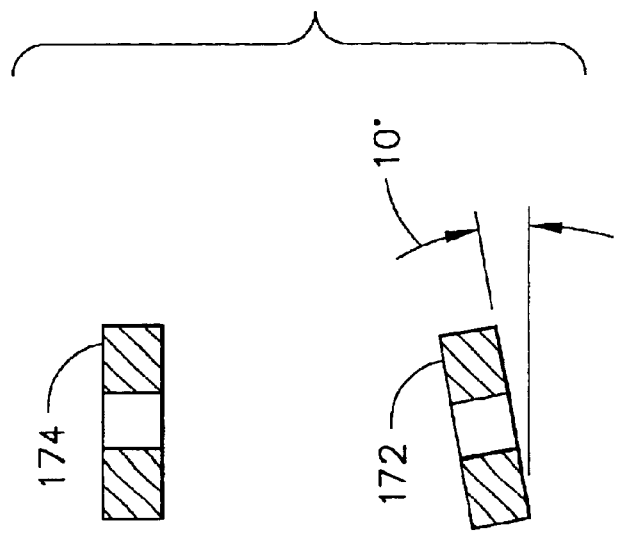
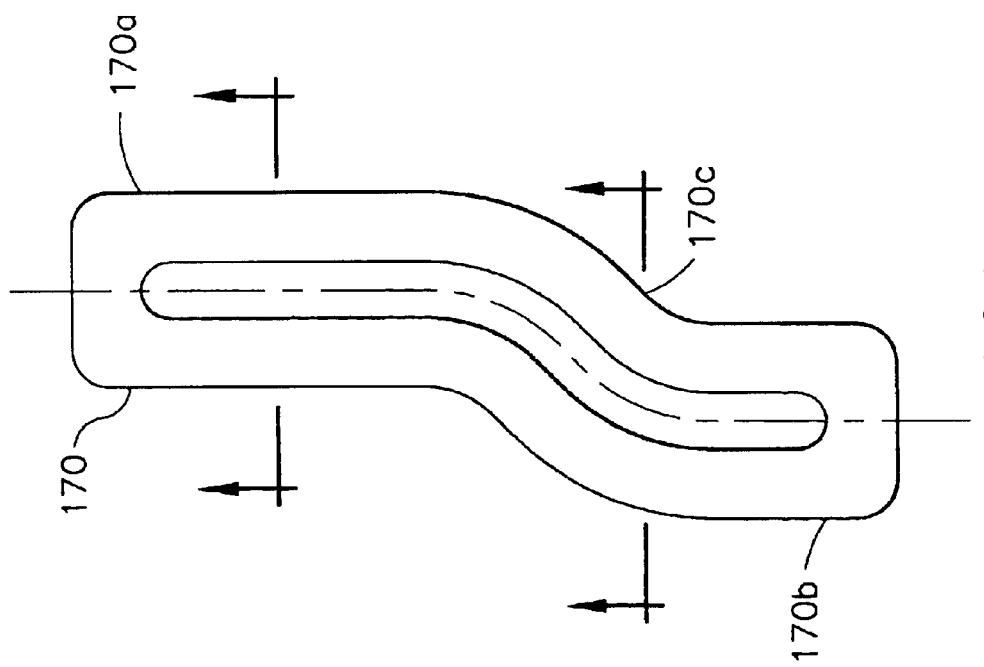
FIG. 10B
FIG. 10A

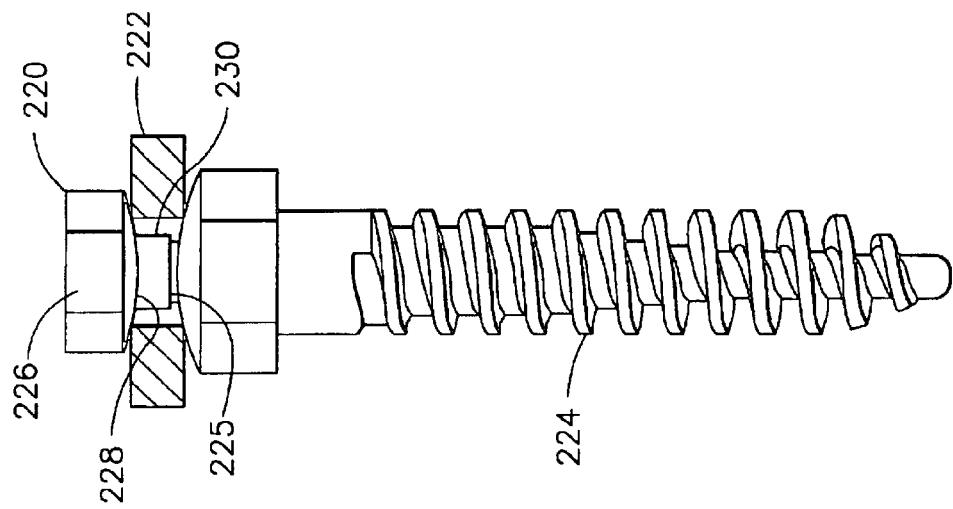
FIG. 14
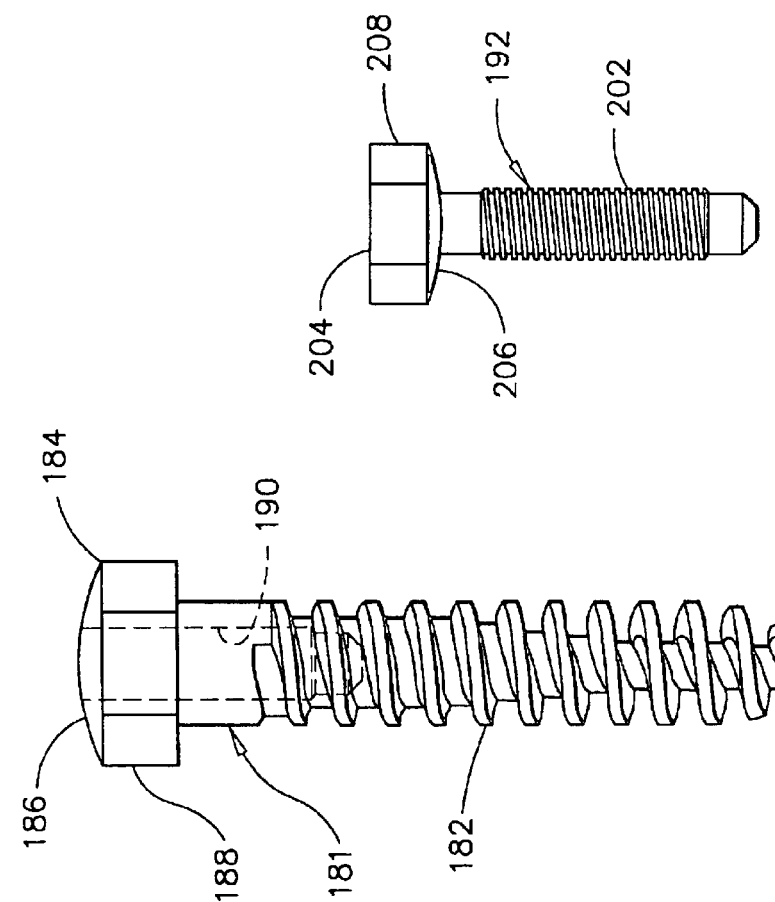
FIG. 13
FIG. 12

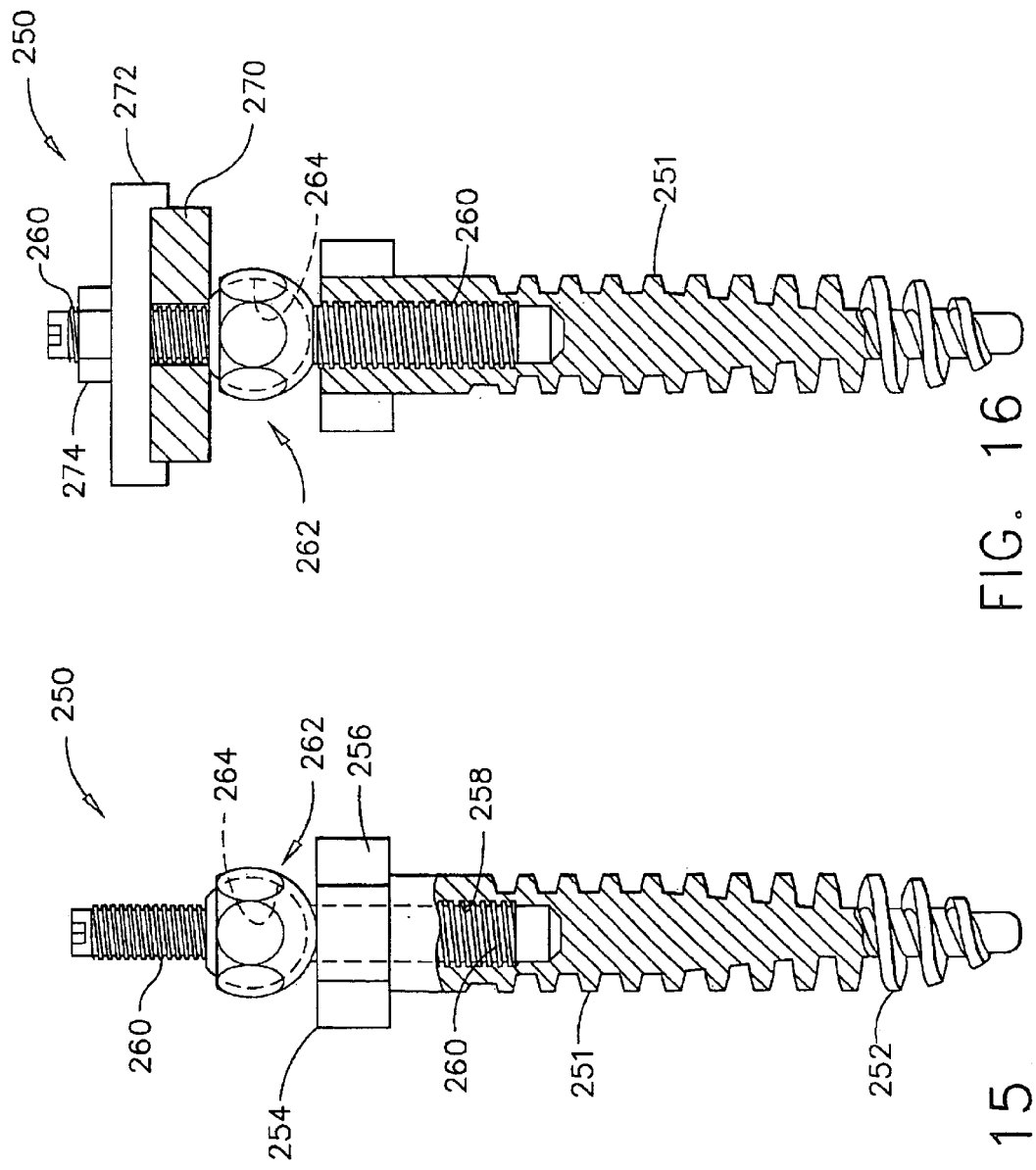

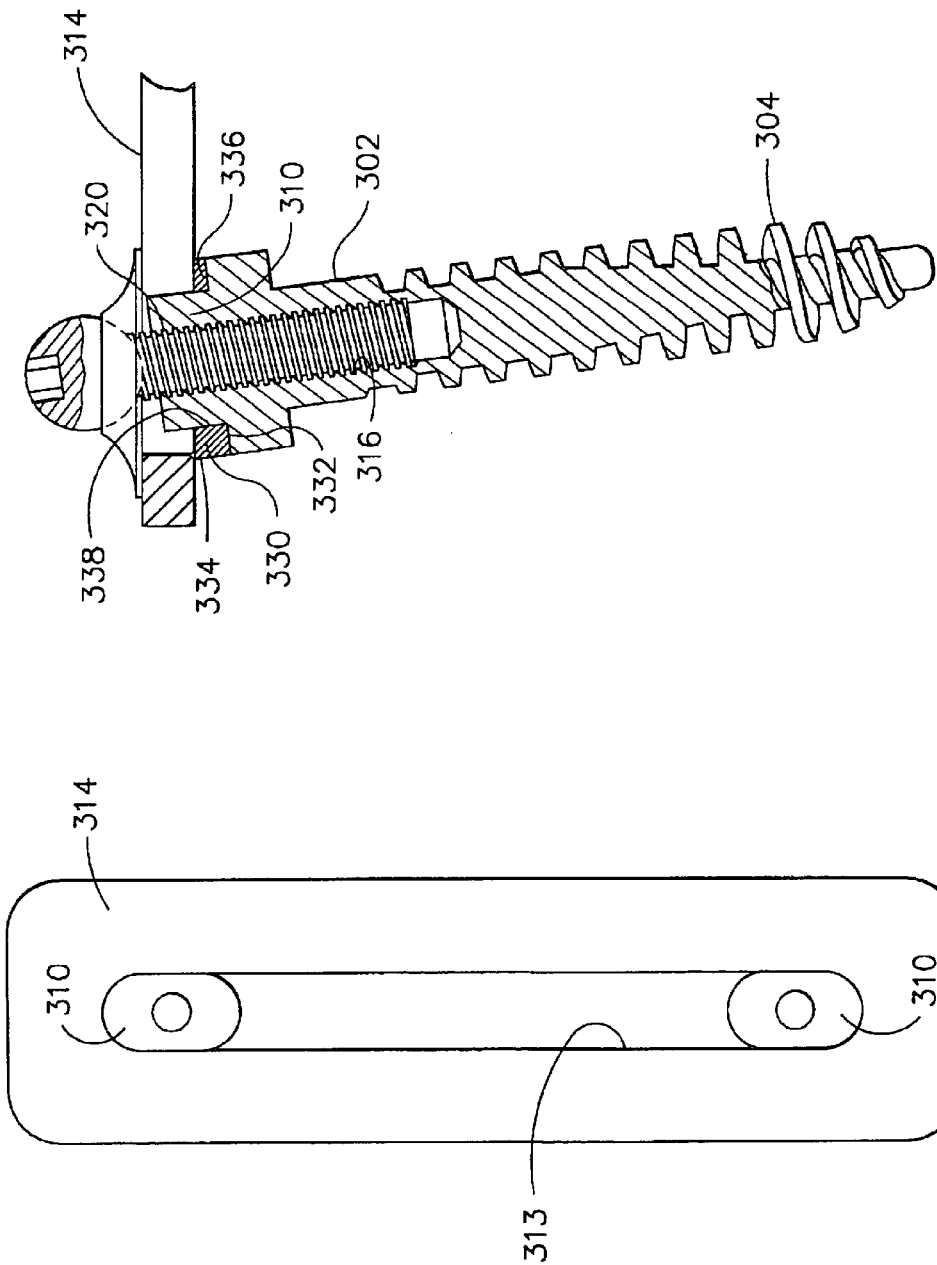

ANATOMIC POSTERIOR LUMBAR PLATE

CROSS REFERENCE TO RELATED APPLICATIONS

This application claims benefit from U.S. Provisional Patent Application Ser. No. 60/279,157, filed Mar. 27, 2001, which application is incorporated herein by reference.

BACKGROUND OF THE INVENTION

1. Field of the Invention

This invention relates generally to devices for use in spinal surgery, and, in particular, to an anatomic posterior lumbar plate which is implantable within a patient for stabilization of the spine.

2. Description of the Related Art

Eighty-five percent of the population will experience low back pain at some point. Fortunately, the majority of people recover from their back pain with a combination of benign neglect, rest, exercise, medication, physical therapy, or chiropractic care. A small percent of the population will suffer chronic low back pain. The cost of treatment of patients with spinal disorders plus the patient's lost productivity is estimated at 25 to 100 billion dollars annually.

Seven cervical (neck), 12 thoracic, and 5 lumbar (low back) vertebrae form the normal human spine. Intervertebral discs reside between adjacent vertebra with two exceptions. First, the articulation between the first two cervical vertebrae does not contain a disc. Second, a disc lies between the last lumbar vertebra and the sacrum (a portion of the pelvis).

Motion between vertebrae occurs through the disc and two facet joints. The disc lies in the front or anterior portion of the spine. The facet joints lie laterally on either side of the posterior portion of the spine. The osseous-disc combination of the spine coupled with ligaments, tendons, and muscles are essential for spine function. The spine allows movement (flexation, lateral bending, and rotation), supports the body, and protects the spinal cord and nerves.

The disc changes with aging. As a person ages the water content of the disc falls from approximately 85 percent at birth to 70 percent in the elderly. The ratio of chondroitin sulfate to keratin sulfate decreases with age. The ratio of chondroitin 6 sulfate to chondroitin 4 sulfate increases with age. The distinction between the annulus and the nucleus decreases with age. These changes are known as disc degeneration. Generally disc degeneration is painless.

Premature or accelerated disc degeneration is known as degenerative disc disease. A large portion of patients suffering from chronic low back pain is thought to have this condition. As the disc degenerates, the nucleus and annulus functions are compromised. The nucleus becomes thinner and less able to handle compression loads. The annulus fibers become redundant as the nucleus shrinks. The redundant annular fibers are less effective in controlling vertebral motion. The disc pathology can result in: 1) bulging of the annulus into the spinal cord or nerves; 2) narrowing of the space between the vertebra where the nerves exit; 3) tears of the annulus as abnormal loads are transmitted to the annulus and the annulus is subjected to excessive motion between vertebra; and 4) disc herniation or extrusion of the nucleus through complete annular tears. Disc herniation can also cause arthritis of the facet joints, which, in turn may cause back pain.

The problems created by disc degeneration, facet arthritis, and other conditions such as spondylolysis, spondylolisthesis, scoliosis, fracture, tumor, or infection are frequently treated by spinal fusion. Such problems may include pain in the back or legs, nerve injury, risk of future nerve injury, or spinal deformity. The goal of spinal fusion is to successfully "grow" two or more vertebrae together. To achieve this, bone from the patient's body (spine or iliac crest) or from cadavers, is grafted between vertebrae. Alternatively, bone graft substitutes, such as hydroxyapatite and bone morphogenetic protein, may be used. The bone graft is placed between the vertebrae in the disc space and/or over the posterior elements of the vertebrae (lamina and transverse processes). The surgeon scrapes the vertebrae to create bleeding. Blood flows into the bone graft. The scraped bone, blood clot (hematoma), and the bone graft simulates a fracture. As the patient heals, the "fracture" causes the vertebrae to be fused and heal together.

Spinal instrumentation may be placed onto or into the spine to immobilize the vertebrae that are going to be fused. Immobilization leads to a higher fusion rate and speeds a patient's recovery by eliminating movement. The use of spinal fixation plates or rods for correction of spinal deformities and for fusion of vertebrae is well known. Typically, a rigid plate is positioned to span bones or bone segments that need to be immobilized with respect to one another. Bone screws may be used to fasten the plate to the bones. Spinal plating systems are commonly used to correct problems in the lumbar and cervical portions of the spine, and are often installed posterior or anterior to the spine.

One technique of treating these disorders is known as surgical arthrodesis of the spine. This can be accomplished by removing the intervertebral disk and replacing it with bone and immobilizing the spine to allow space to connect the adjoining vertebral bodies together. The stabilization of the vertebrae to allow fusion is often assisted by a surgically implanted device to hold the vertebral bodies in proper alignment and allow the bone to heal, much like placing a cast on a fractured bone. Such techniques have been effectively used to treat the above described conditions and in most cases are effective at reducing the patient's pain and preventing neurologic loss of function.

Several types of anterior spinal fixation devices are currently in use. One technique involves placement of screws completely through the vertebral body, called bicortical purchase. The screws are placed through a titanium plate but are not attached to the plate. This device is difficult to place, and over-penetration of the screws can result in damage to the spinal cord. The screws can back out of the plate into the surrounding tissues as they do not fix to the plate. Several newer generation devices have used a unicortical purchase of the bone, and in some fashion locking the screw to the plate to provide stability and secure the screw from backout. Problems have resulted from over rigid fixation and stress shielding, resulting in nonunion of the bony fusion, chronic micromotion during healing, resulting in stress fracture of the fixation device at either the screw to the plate resulting in screw backout, or inadequate fixation strength and resultant collapse of the graft and angulations of the spine.

Another technique involves formation of a medical construct using surgical rods and connectors. Such systems include a pair of rods which are placed on opposite sides of the portion of the spine which is intended to be fused. Pedicle, lateral, and oblique mounting means are used to secure the rods relative to the desired portion of the spine which will be fused by the fixation system. However, this construct extends outwardly further than a plate/screw system, potentially affecting the surrounding muscle, and causing pain to the patient.

A typical device which is used for spinal fixation is taught in U.S. Pat. No. 4,611,581. This device consists of a simple plate having a series of openings for receiving threaded portions of force transmitting members which securely lock in a part of the bone of the vertebra in which they are mounted and a threaded portion which projects outwardly from the vertebrae. The vertebra is pulled into the desired relationship with adjacent vertebrae by tightening a nut on the outwardly projecting end portion of the force transmitting member.

Another typical device used is shown in U.S. Pat. No. 6,306,136. This patent discloses an implant which is used particularly as an anterior cervical plate, having a solid plate consisting of two sliding parts, each of which has holes for anchoring screws in two adjacent vertebrae. The sliding parts are provided with a screw and slot for limiting the sliding travel between the parts.

Another vertebrae connecting plate is taught in U.S. Pat. No. 5,147,361. This plate has a small thickness, and uses set screws which are screw engaged in threaded holes within the connecting plate to prevent any loosening of the screws within the plate.

One problem that sometimes arises in the use of known plate systems is when the points on the vertebrae defined by the screws are not collinear, i.e. they do not line up in a straight line. This creates a problem when the openings in the plate do not align with the position where the screws are to be inserted. The plate must then be contoured intraoperatively, which is often a difficult and time consuming task. A device is taught in U.S. Pat. No. 6,336,927 that attempts to overcome this problem. This device includes a plurality of link members which can be screwed to adjacent vertebrae in chain-like fashion using pedicle screws that are not collinear with each other. The link members can be used to subdivide multiple nonlinear pedicle fixation points into units of two adjacent points, which two points can be interconnected using a single link member.

Still another problem which arises when using spinal plates is the differences in spinal curvature depending on the location of the vertebrae to be stabilized. U.S. Pat. No. 5,647,872 addresses this problem by providing a preformed plate having a spine opposing face incorporating two patterns or components of curvature.

SUMMARY OF THE INVENTION

It is therefore an object of the present invention to provide a plate system for spinal surgery which comfortably fits a patient's anatomy.

It is a further object of the present invention to provide a plate system which is easily implanted within a patient.

It is a further object of the present invention to provide a plate system which is easily positioned and establishes a secure connection between vertebrae.

It is a still further object of the present invention to provide a plate which is easily adaptable to the lumbar region of the spine.

These and other objects and advantages of the present invention will be readily apparent in the description that follows.

BRIEF DESCRIPTION OF THE DRAWINGS

FIGS. 10A and B show a spinal plate according to the present invention, along with a cross-sectional view;

FIG. 12 shows a plan view, partly in phantom, of a pedicle screw for use in the present invention;

FIG. 13 shows a plan view of an inner screw for use in the present invention;

FIG. 14 shows a plan view of a spinal system of the present invention using an extended nut;

FIG. 15 shows a plan view of a screw locking system according to the present invention;

FIG. 16 shows a plan view of the system of FIG. 15 in the installed position;

FIG. 22 is a top view of the pedicle screw in position with the spinal plate according to the present invention;

FIG. 23 is a fragmentary side view, partly in cross section, of a plate system according to the present invention, using a washer;

DETAILED DESCRIPTION OF THE PREFERRED EMBODIMENTS

Figure 1:
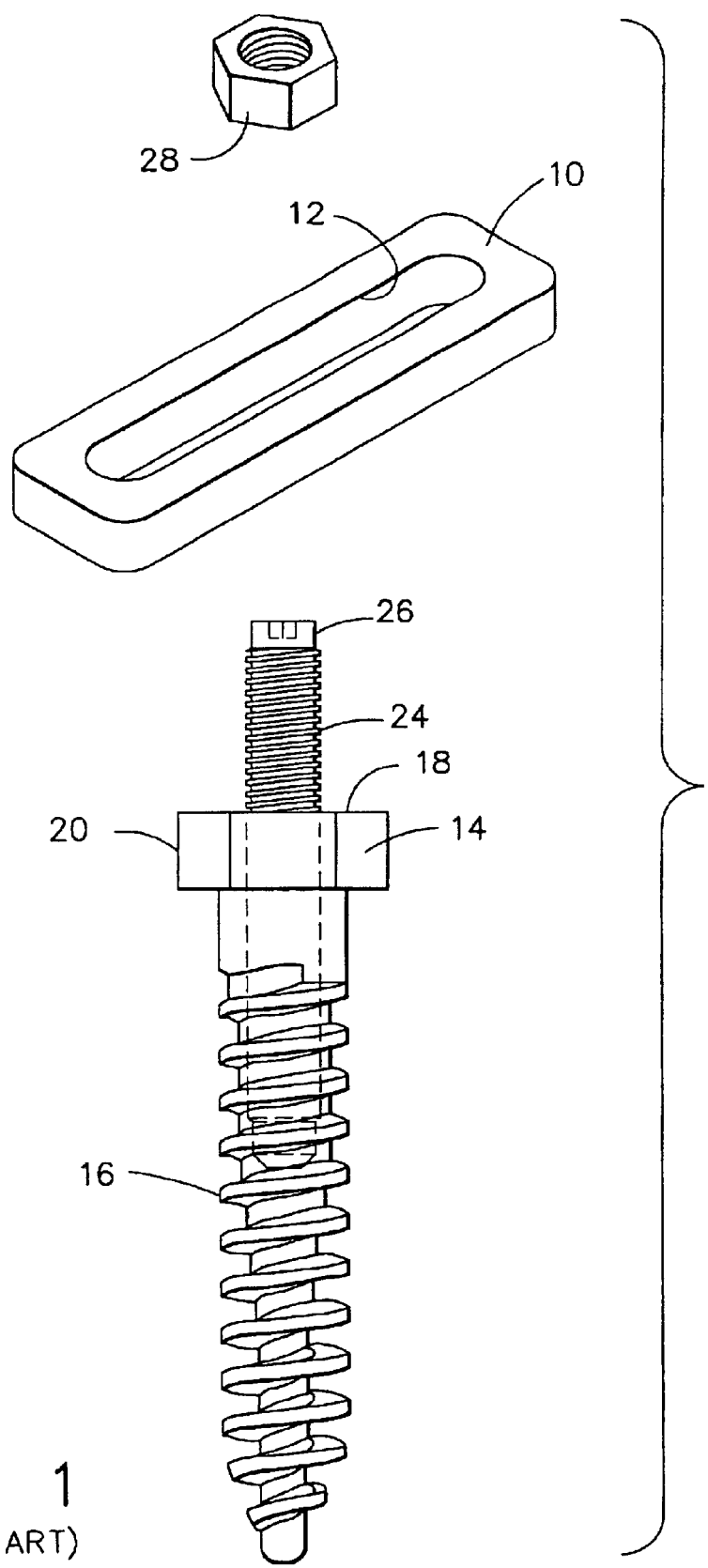
FIG. 1 is an exploded view of a spinal plate system of the prior art.
Figure 2:
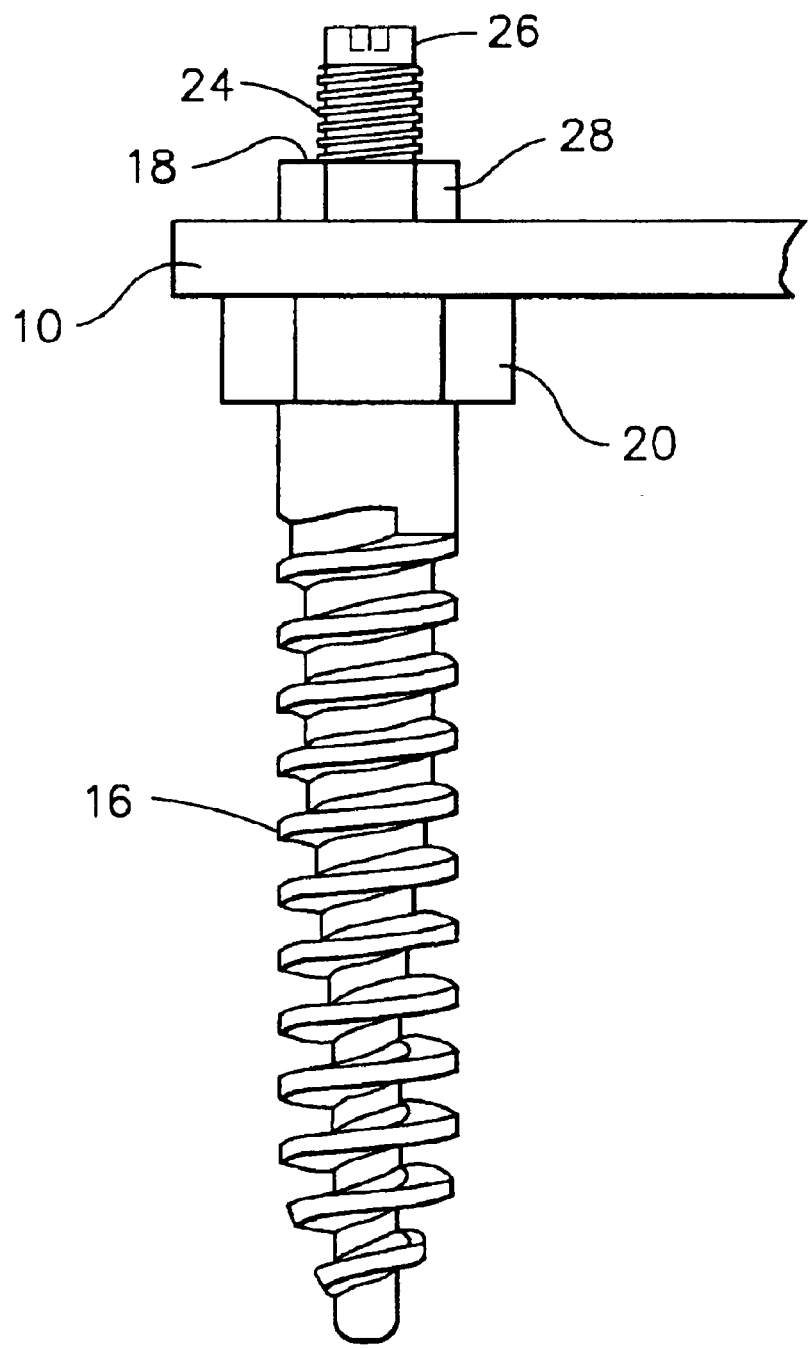
FIG. 2 is an assembled view of the system of FIG. 1.

FIGS. 1 and 2 represent a typical prior art plate system currently used for spinal stabilization. Referring now to FIG. 1, there is shown a spinal plate 10. Plate 10, which is generally rectangular or elliptical in shape, contains an opening 12 in its central portion. A pedicle screw 14 is shown having a threaded shaft 16 and an upper region 18. Screw 14 contains an extended section 20 shaped to easily receive a tool for threading screw 14 into the bone. Upper region 18 is shown having a threaded section 24 and a head 26. Head 26 is of a lesser diameter than threaded section 24 such that a nut 28 can be threaded onto threaded portion 24 of inner screw 22.

Referring now to FIG. 2, the plate system of FIG. 1 is shown in its assembled position. Plate 10 is positioned on pedicle screw 14 through opening 12 after it has been installed into the bone such that section 20 contacts the bottom side of plate 10. Nut 28 is then threaded onto threaded shaft 24 and against the upper surface of plate 10 to secure the system. Generally, several of pedicle screws 14 are used to secure plate 10 to vertebrae of the spine for stabilization.

One problem that often occurs when using these prior art plates is that the preferred locations of the pedicle screws for attaching the plate to the spine do not lie collinearly. For example, the pedicle screw in L5 often lies lateral to the screws in L4 and S1, forcing the L5 pedicle screw to fit into a rectangular plate and risking fracture of the L5 pedicle screw due to stress.

Figure 4:
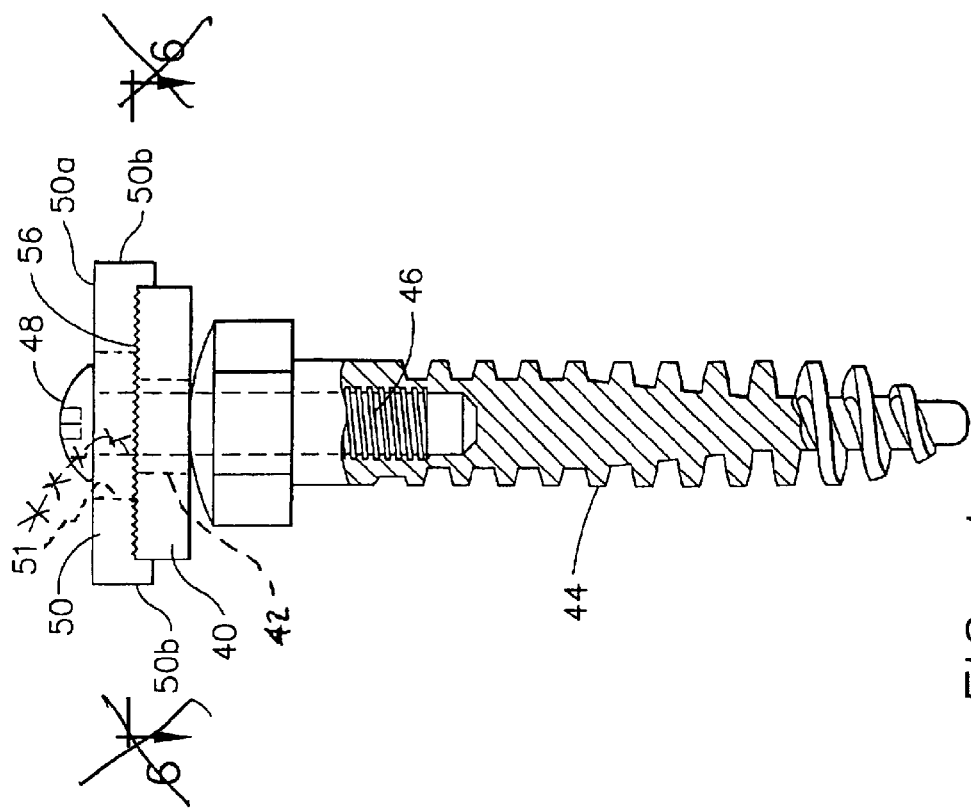
FIG. 4 is a side view, partly in cross section, of the system of FIG. 3.
Figure 3:
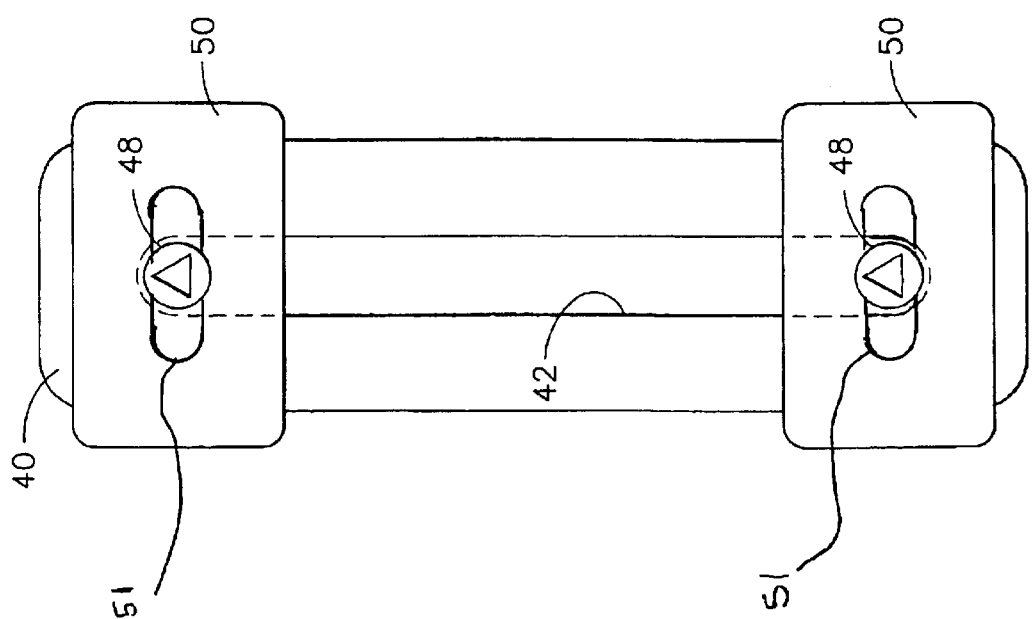
FIG. 3 is a plan view of a spinal plate system according to the present invention.

A solution to this problem is to enlarge the opening in the spinal plate and use a washer to position the pedicle screw within the opening. Referring now to FIGS. 3 and 4, there is shown a plate 40 having an opening 42 which is wider than the opening in prior art plates. Pedicle screws 44 have been placed into the proper vertebrae, and inner screws 46, each having a head 48, have been threaded into the interior section of pedicle screws 44 to hold plate 40 securely in place. Between head 48 of each pedicle screw 46 and plate 40, there is positioned a washer 50. Washer 50 contains a flat section 50a and side sections 50b, which depend in a perpendicular direction downwardly from section 50a, along with an opening 51 that screw 46 passes through. Opening 51 may be slotted such that inner screw 46 may be accurately positioned for insertion. Sections 50b overhang the edges of plate 40 such that inner screw 46 can be optimally positioned within opening 42 for holding plate 40 in its proper location without putting undue stress on pedicle screws 44. To assist in the stable positioning of washer 50 along plate 40, a frictional surface 56 may be added to the top surface of plate 40 and the bottom surface of washer 50. Plate 40 is particularly suited for use as a posterior lumbar plate. Installation of plate 40 is easily accomplished, as it is top loading and top tightening.

Figure 6:
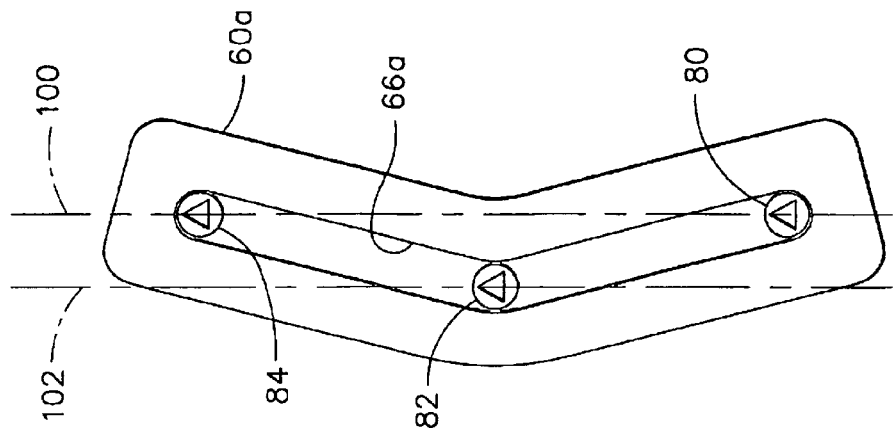
FIG. 6 is a plan view of one of the plates shown in FIG. 5 in the installed position.
Figure 5:
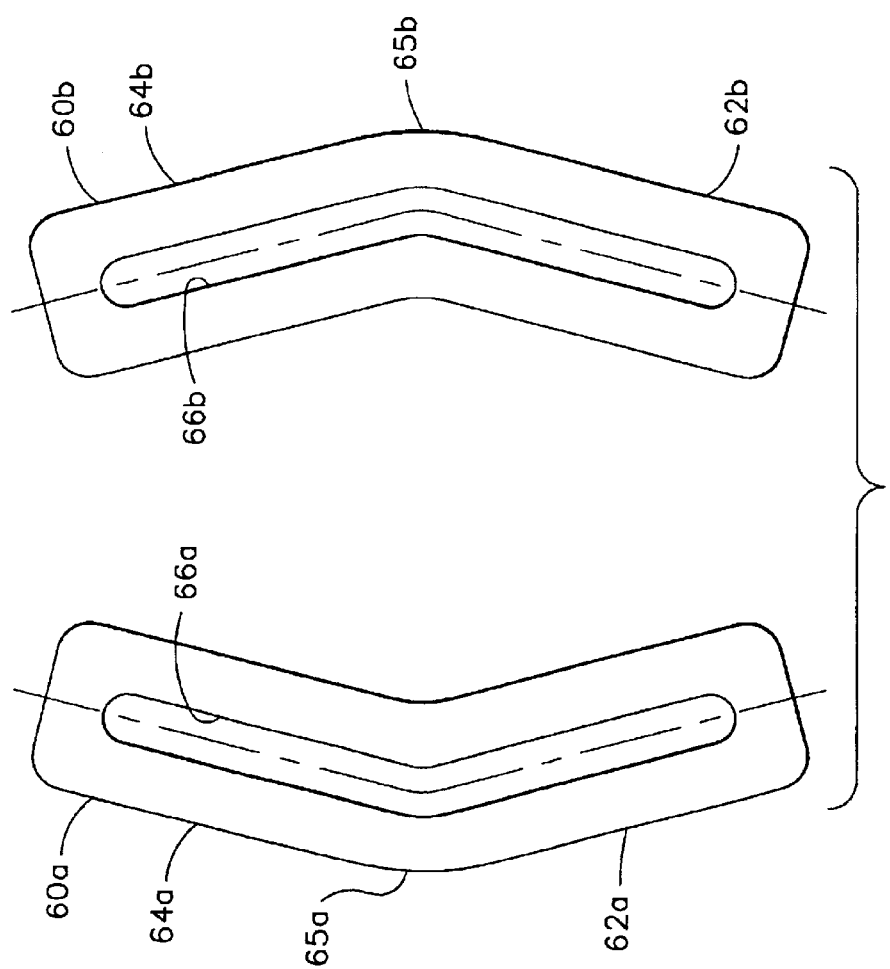
FIG. 5 is a plan view of several spinal plates manufactured according to the present invention.

Another solution to the problem of non-collinearity of the screw placement in the lower lumbar region of the spine involved the use of specially shaped spinal plates. FIGS. 5 and 6 show these plates. Referring now to FIG. 5, a pair of nonlinear plates 60a, 60b are shown having a first linear section 62a, 62b and a second linear section 64a, 64b connected by an angled section 65a, 65b. Plates 60a, 60b contain an opening 66a, 66b which runs along the length of the plates. Plate 60a is designed to be implanted on the left side of the spinal column, while plate 60b is designed to be implanted on the right side. One of plates 60a, 60b is preferably used in spine fusion procedures spanning two or more levels which include L5 or L5 and S1. FIG. 6 shows a two level fusion plate, which spans this region of the spine. Plate 60a is shown in position implanted on the spine with a pedicle screw 80 shown secured to S1, a pedicle screw 82 secured to L5, and a pedicle screw 84 secured to L4.

Figure 7:
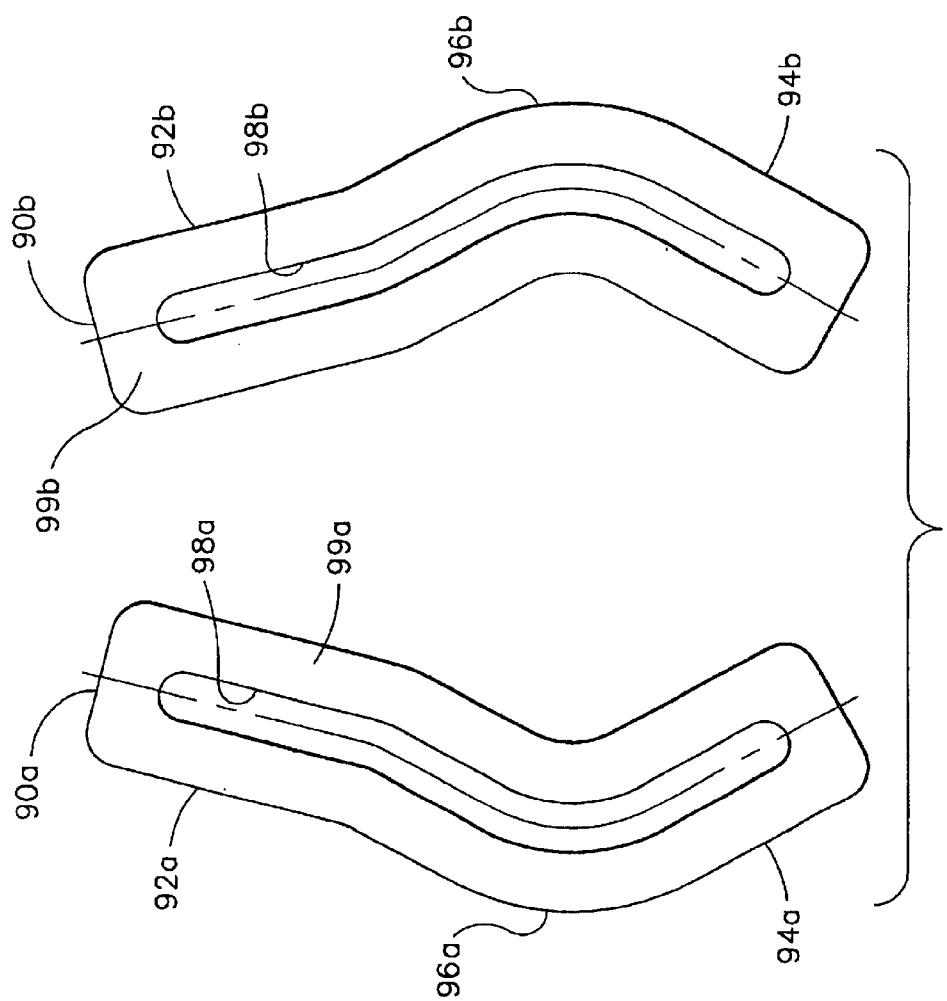
FIG. 7 is a plan view of another set of spinal plates manufactured according to the present invention.

FIG. 7 shows a set of plates which is designed for use in a three level fusion. A pair of non-linear plates 90a, 90b are shown having a first linear region 92a, 92b and second linear region 94a, 94b joined by a curved region 96a, 96b. Plates 90a, 90b contain an opening 98a, 98b which runs along the length of the plate. Note that the cephalad portion 99a, 99b of regions 94a, 94b which lie above the L4 vertebra which, when implanted on the spine, is essentially linear. If a plate is desired for use for a 4 or 5 level fusion, a plate having portion 99a, 99b extended linearly may be constructed.

Referring again to FIG. 6, the non-collinearity of the pedicle screws can be clearly seen. A line 100 is shown extending through screw 80 at S1 and screw 84 at L4, while a parallel line 102 is shown passing through screw 82 at L5. The average distance between parallel lines 100 and 102 varies between 5 mm and 7 mm. The average distance between S1 and L5 is approximately 3 cm, while the average distance between L5 and L4 is approximately 3.5 cm.

Figure 8:
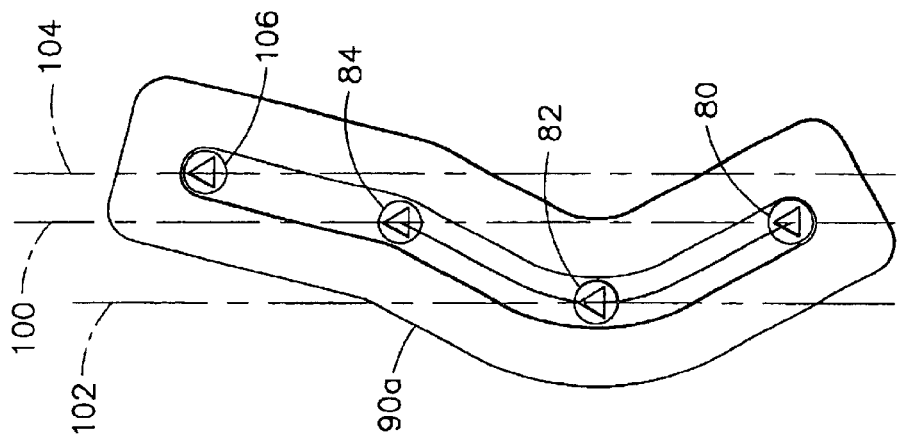
FIG. 8 is a plan view of one of the plates shown in FIG. 7 is the installed position.

Referring now to FIG. 8, the non-collinearity of a three-level plate is shown. Line 100 extends through screw 80 at S1 and screw 84 at L4. Parallel line 102 extends through screw 82 at L5, while another parallel line 104 extends through a pedicle screw 106 which is fastened at L3. The distance between line 100 and line 102 is an average of 5 mm to 7 mm, while the distance between line 100 and line 104 is approximately 3 mm to 5 mm. Thus, it will be necessary to offer different size plates which would be used in surgery depending on the particular sizes applicable to different patients. For example, plates 60a, 60b and plates 92a, 92b could be available with either 3 mm, 5 mm, or 7 mm between the L5/S1 offset lines, and 3 mm and 5 mm between the L4/L3 offset line, or can be available for any combination thereof.

Figure 9:
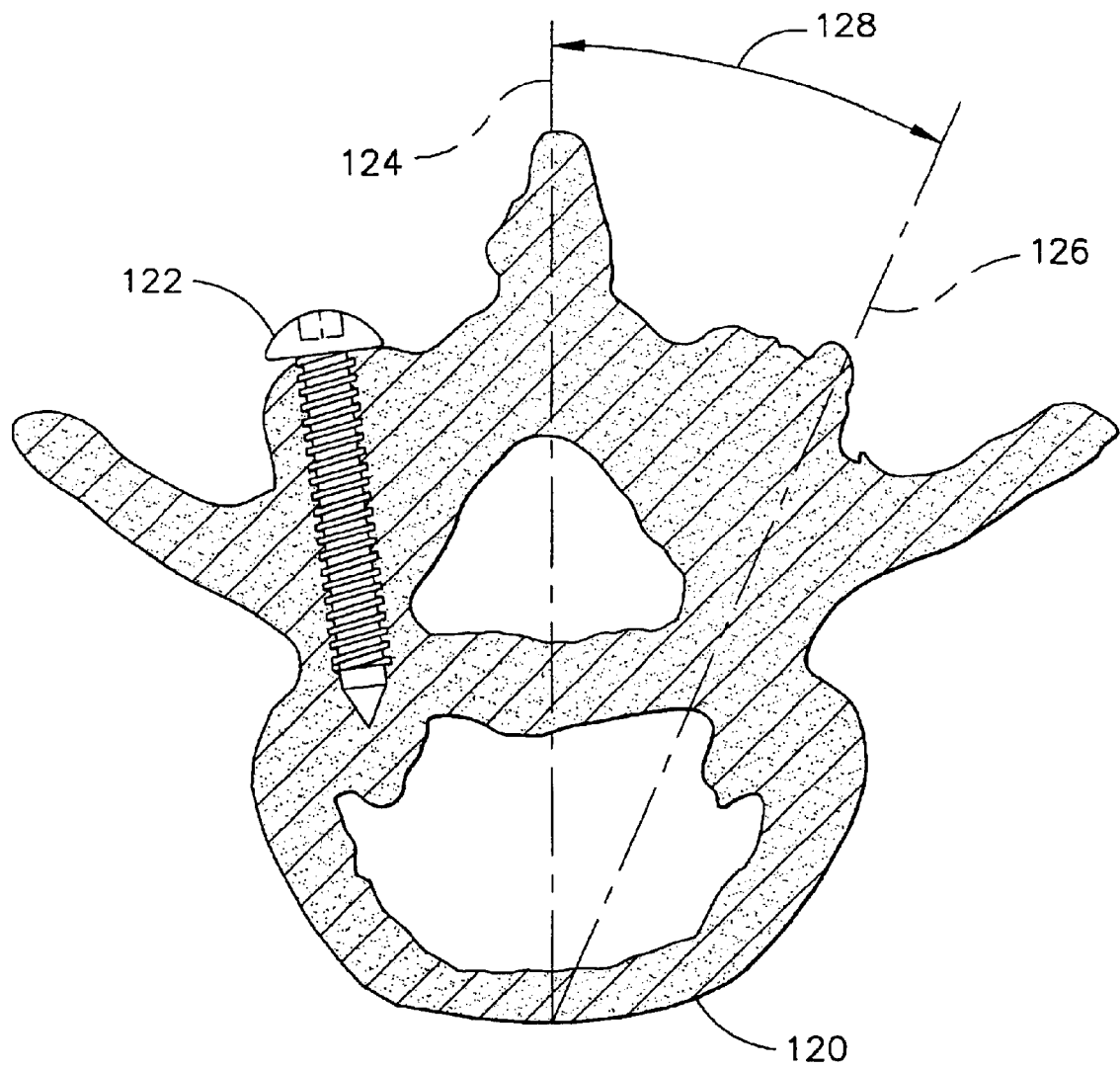
FIG. 9 is a cross-sectional view of a vertebra showing the relative position of a pedicle screw installed according to the present invention.

Another problem which arises in the implantation of spinal plates involves the angle of pedicle screws. Pedicle angulation increases in the caudal portion of the spine, as is shown in FIG. 9. Referring to FIG. 9, there is shown a vertebra 120 having a pedicle screw 122 inserted. A line 124 passes through the center of vertebra 120, while a second line 126 extends angularly from center line 124 from vertebra 120. An angle 128, called the transverse pedicle angle, defines the angular relationship between lines 124 and 126. Angle 128 changes for each vertebra in the caudal area. For example, the average angle 128 for L2 is 12°; for L3, it is 14°; for L4, it is 18°; for L5, it is 30°; and for S1, it is greater than 30°. Unfortunately, the angle of screw insertion does not always match the transverse pedicle angle. Therefore, when the angle of screw insertion is significantly different from the plate angle, the inner screws can be difficult to insert through the plate, and as the screws are tightened, the pedicle screw alignment in the bone can be changed and could conceivably be forced out of the lateral portion of pedicle as the inner screw is tightened.

Several solutions to address this problem are proposed in the present invention. One solution is to increase the width of the opening within the spinal plate through which the inner screw is inserted into the pedicle screw. This can be accomplished by use of washer 50 which is shown and described with respect to FIGS. 3 and 4. By using washer 50, the central opening with the spinal plate can be enlarged as washer 50 spans across the opening and the inner screw can be inserted into the pedicle screw with greater leeway.

Another solution to this problem involves a twisting of the spinal plate in the area of L5. FIGS. 10A and B show a spinal plate having this twist. Referring now to FIGS. 10A and 10B, a spinal plate 170 is shown having an upper linear section 170a and a lower linear section 170b which are connected by a curved section 170c. In use, section 170c is positioned at L5 along the spine. At this section, plate 170 is twisted from the horizontal at a 10° angle, as can been seen at 172 in the cross-sectional view FIG. 10B, while plate 170 is flat at 170a, as seen at 174 in FIG. 10B. In this manner, the upper surface of the pedicle screw can align better with the bottom surface of plate 170 such that the inner screw can be inserted without additional stress to the pedicle screw/inner screw coupling.

Figure 11A:
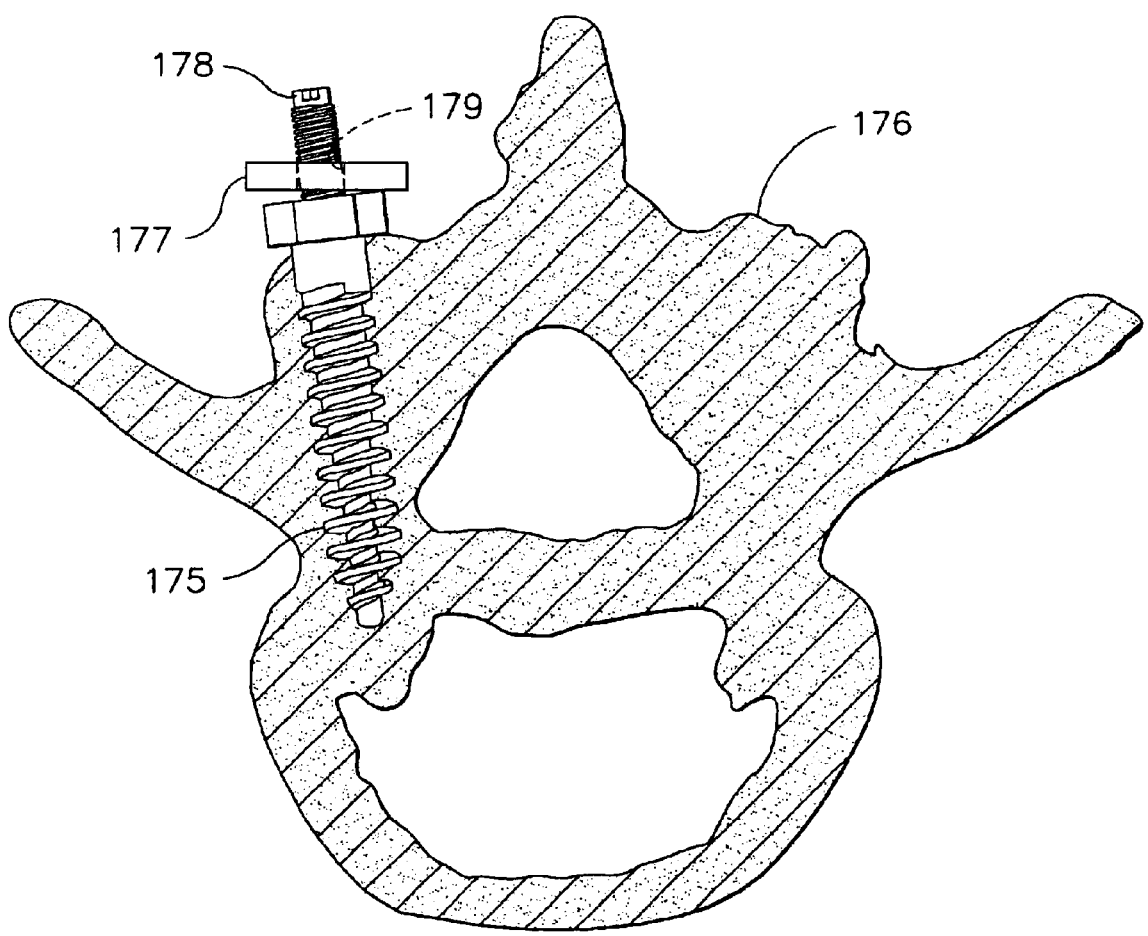
FIGS. 11A–C, taken together, represent a sequence of tightening a spinal plate into position.
Figure 11B:
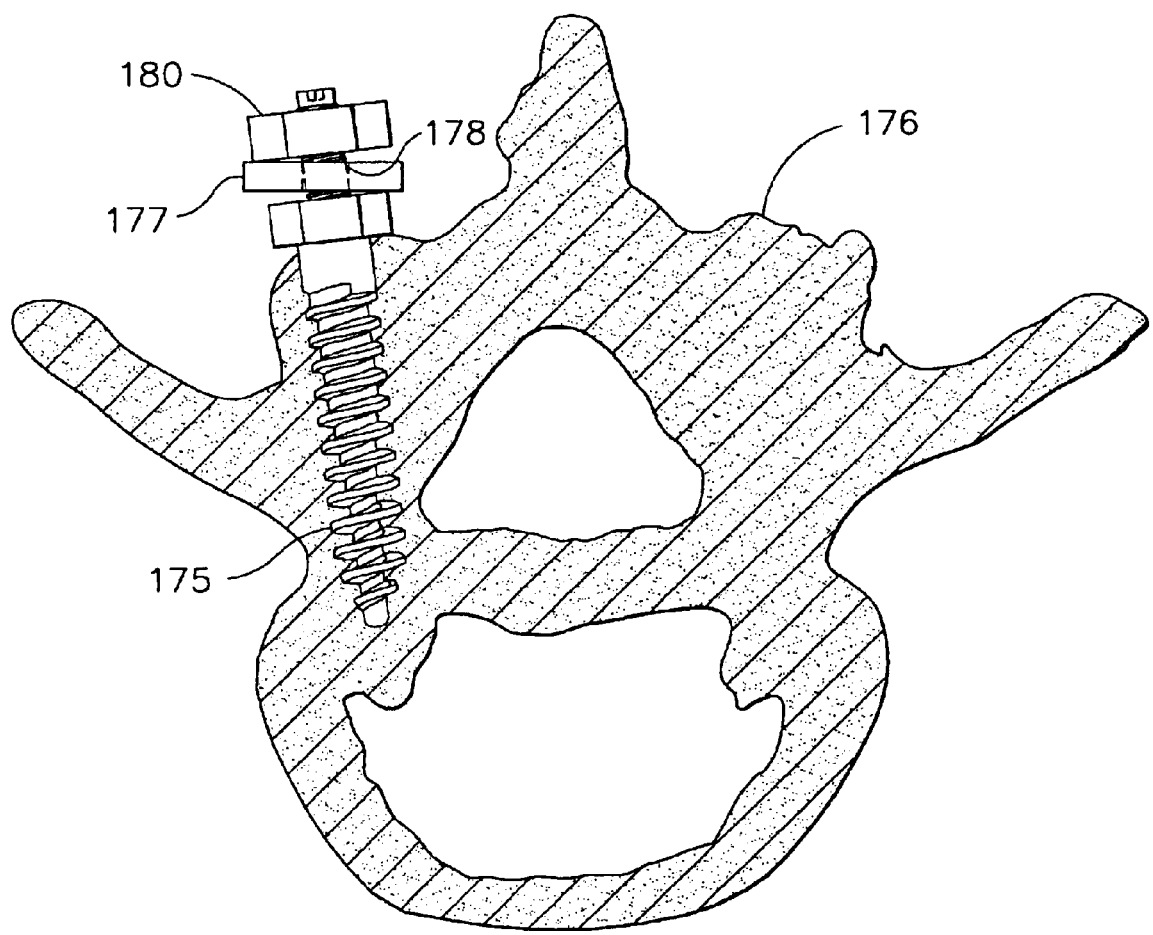
Figure 11C:
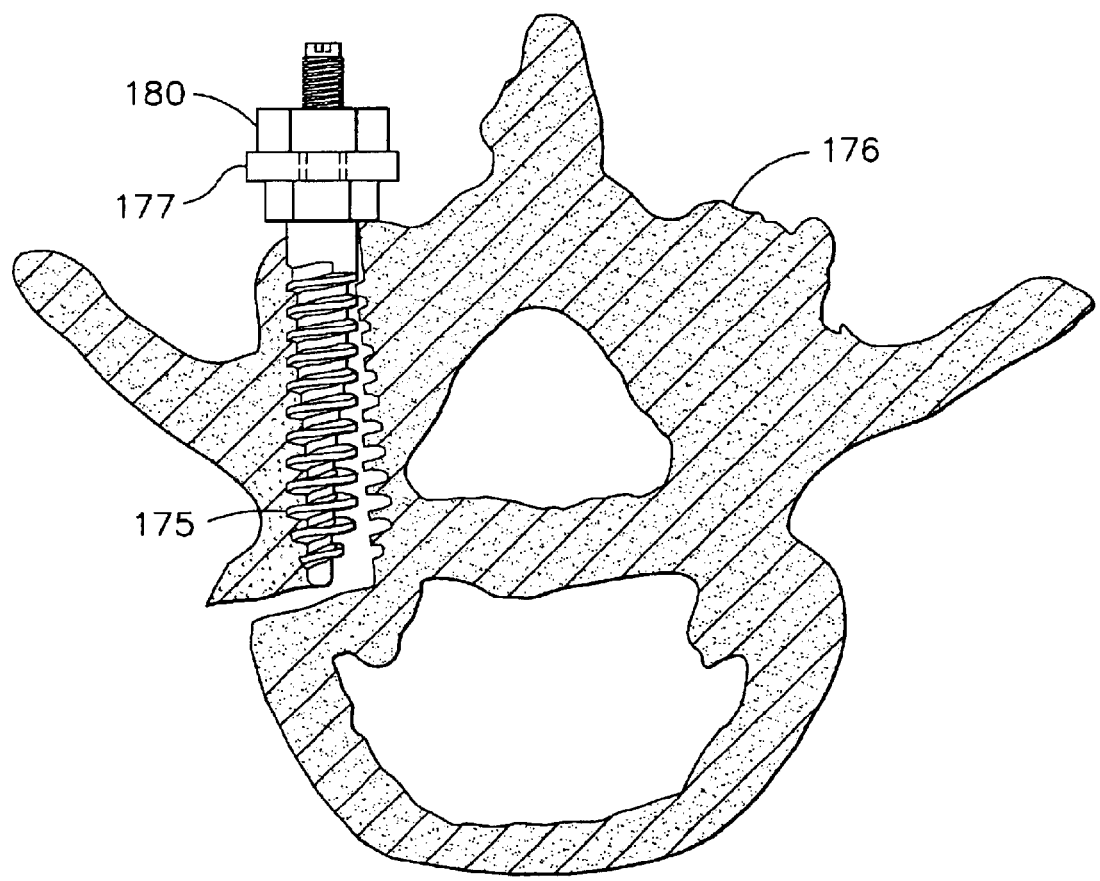

If the angle of the screw insertion is significantly different from the plate angle, the inner screw can be difficult to insert through the plate, and as the screw is tightened the pedicle screw alignment in the bone can be changed, even to the point where pedicle screw extends from the bone. This scenario can be seen in FIGS. 11A–C. Referring now to FIG. 11A, a pedicle screw 175 has been inserted into a vertebra 176 and a plate 177 is tightened into position by an inner screw 178. It can be seen that screw 178 contacts the sides of opening 179 through plate 177, as screw 178 is at an angle to plate 177. In FIG. 1B, a nut 180 is placed onto screw 178 and is torqued to fasten plate 177 into place. As nut 180 is screwed onto screw 178, the stress placed on pedicle screw 175 is great enough to cause screw 175 to be forced through the lateral portion of vertebra 176, as can be seen in FIG. 11C.

A solution for reducing this problem involves the use of a pedicle screw having a rounded head. Referring now to FIG. 12, there is shown a pedicle screw 181 for use in the present invention. Pedicle screw 181 contains a threaded portion 182 which is screwed into bone, and a head portion 184. Head portion 184 consists of a spherical top portion 186 and an outwardly extending lower portion 188. Portion 188 is preferably hexagon shaped, or a similar structure, such that it accommodates a wrench or similar tool to insert threaded portion 182 into the bone. Screw 181 also includes a hollow threaded interior portion 190.

When pedicle screw 181 is installed in bone and a spinal plate inserted over it, and an inner screw 192 is threaded into interior portion 190, spherical top portion 186 of screw 181 allows the plate to be tightened into position without creating undue stress on the system. The thread interaction between inner screw 192 and interior portion 182 of pedicle screw 181 should help lock the two together when torqued to the proper amount. If it is not possible to create enough torque using current inner screws, a special head could be adapted onto the inner screw, as can be seen in FIG. 13. Referring now to FIG. 13, inner screw 192 contains a lower threaded section 202 and a head section 204. Head section 204 further has a spherical lower section 206 and a larger section 208 configured to accommodate a wrench or similar tool which can apply considerable torque to screw 192.

Another device which would ease insertion of a spinal plate system is shown in FIG. 14. Referring now to FIG. 14, an extended nut 220 is used to securely fasten a spinal plate 222 in position on a pedicle screw 224 and an inner screw 225. Nut 220 contains an upper portion 226 configured to accommodate a wrench or similar tool, a central spherical section 228, and a lower cylindrical section 230. Section 230 is configured to be positioned within an opening within plate 222, while section 228 acts to accurately position nut 220 relative to pedicle screw 224 and inner screw 225. Ideally, the length of cylindrical section 230 should be less than the width of plate 222, or plate 222 and a washer, if a washer is to be used.

Still another device which would ease insertion of a spinal plate system is shown in FIG. 15. Referring now to FIG. 15, there is shown a multiaxial screw system 250 including a pedicle screw 251 having a lower threaded section 252 which is shaped to be threaded into bone, and an upper section 254. Upper section 254 contains a lower portion 256 configured to accommodate a wrench for threading screw 251 into the appropriate vertebra. Pedicle screw 251 also has an internally threaded portion 258 for receiving an inner screw 260. A multiaxial seat 262 is threaded onto the threaded portion 252 of pedicle screw 251. Seat 262 has a hollow spherical section 264 which accommodates inner screw 260. In operation, which can be clearly seen in FIG. 16, when a plate 270 is positioned over seat 262 and pedicle screw 251, and inner screw 260 is threaded in position, section 264 of seat 262 allows for a range of motion while inserting inner screw 260 to secure screw 260 safely. A washer 272, as described earlier, can be installed over plate 270 to stabilize system 250, and a nut 274 is tightened to tightly secure system 250 in the proper position. As nut 274 is tightened over plate 270, multiaxial seat 262 locks into position, and system 250 is pulled securely into the proper orientation.

Figure 17:
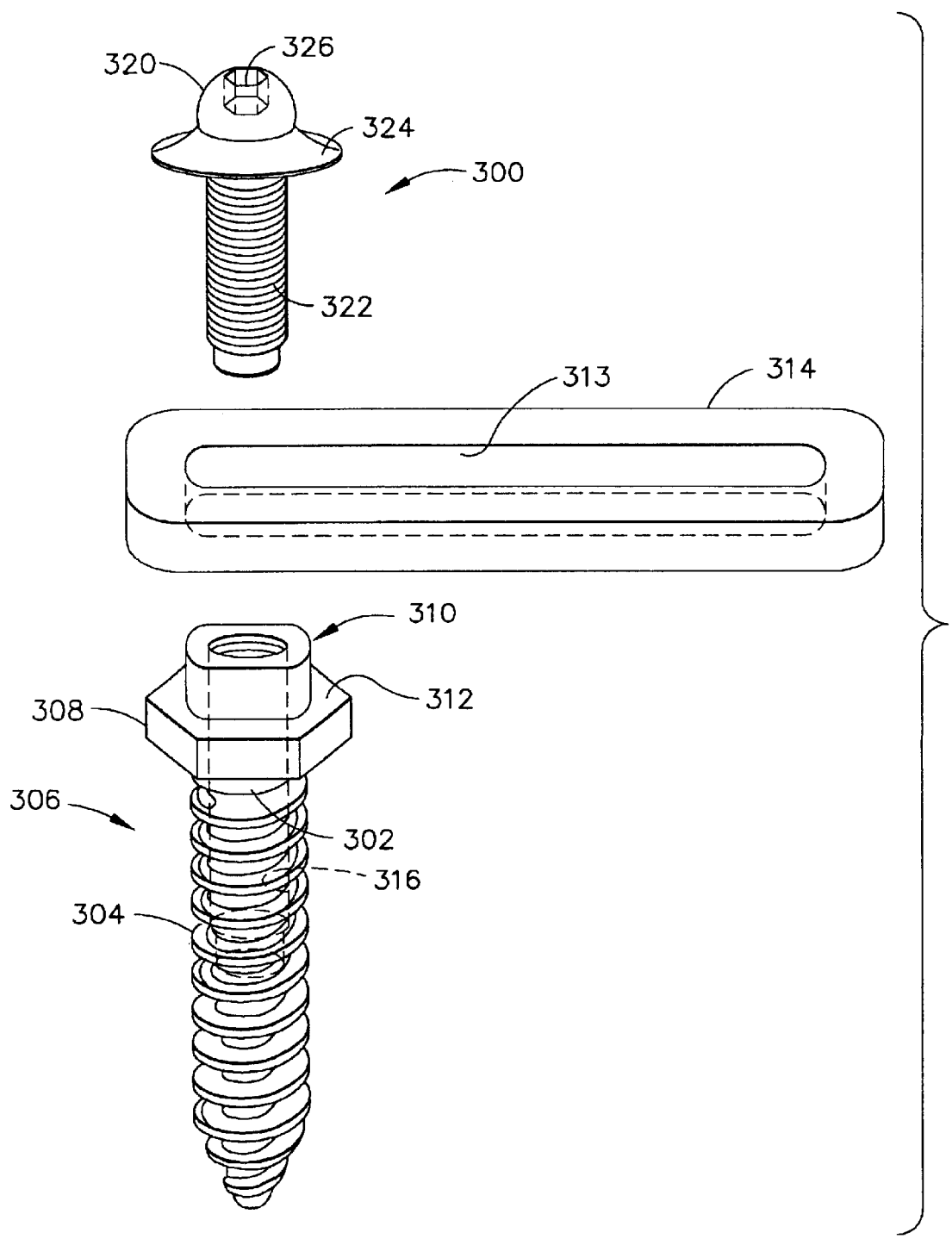
FIG. 17 shows an exploded view of an alternative embodiment of a screw system for use in the present invention.
Figure 19:
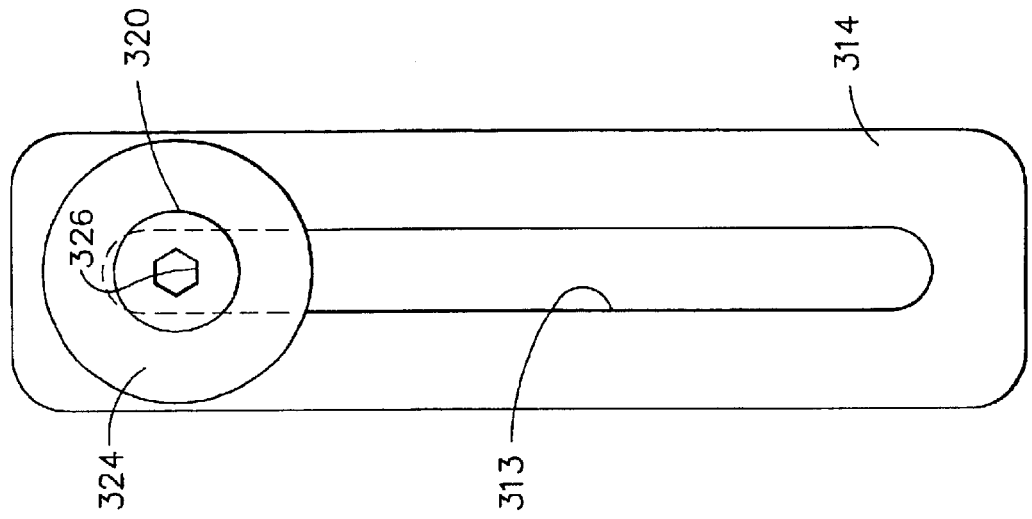
FIG. 19 is a top view of the system shown in FIG. 18.
Figure 18:
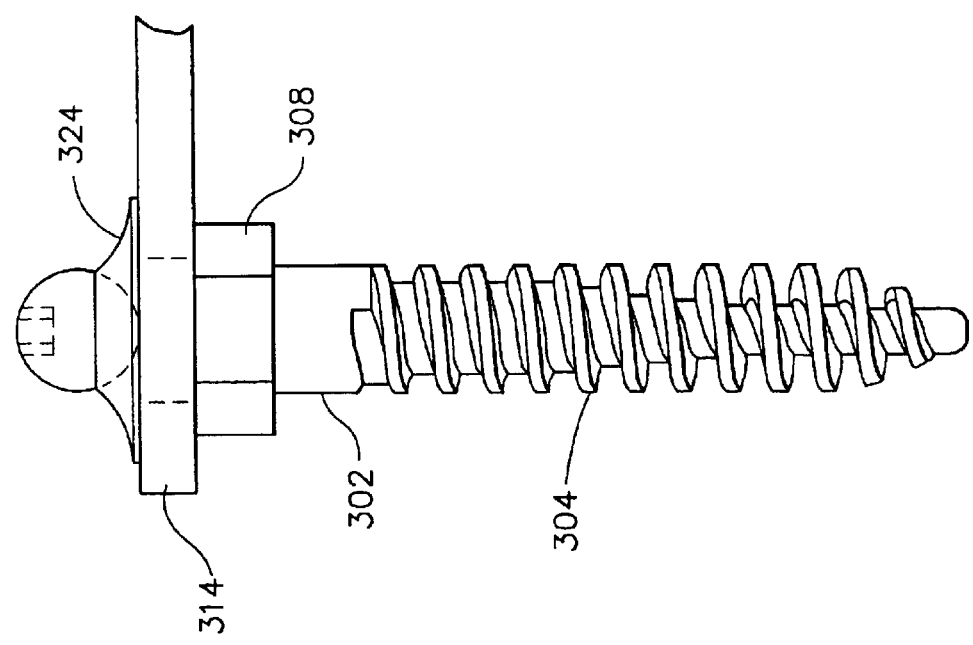
FIG. 18 is a side view of the screw system of FIG. 17 in the assembled position.
Figure 20:
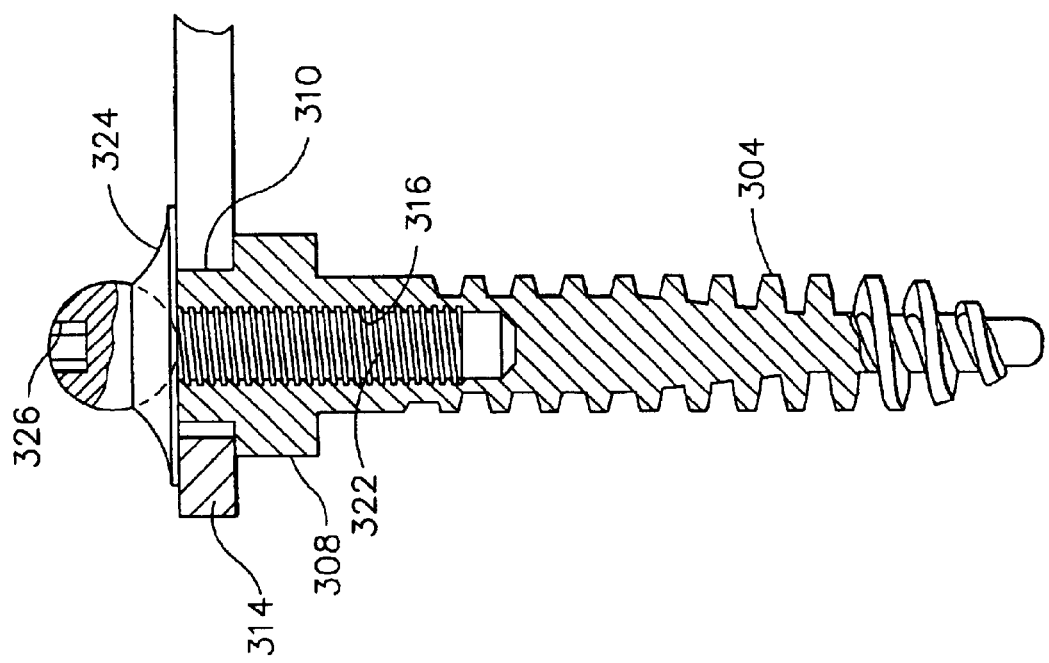
FIG. 20 is a cross-sectional view of the system shown in FIG. 18.

An alternative embodiment of the spinal plate system of the present invention is shown in FIGS. 17–22. Referring now to FIG. 17, there is shown a novel screw system, generally indicated at 300. Screw system 300 includes a pedicle screw 302 having a lower threaded section 304 capable of locking system 300 into bone, and an upper section 306 having an unthreaded portion 308 which is shaped to accommodate a wrench for threading screw 302 into a vertebra. Section 306 also includes an extension 310 which extends from a flat upper surface 312 of portion 308. Extension 310 is preferably elliptical or oval shaped to fit nicely in a slotted opening 313 within a spinal plate 314. Pedicle screw 302 also contains a threaded hollow portion 316 capable of receiving the threaded portion of an inner screw 320. Screw 320 includes a lower threaded portion 322 which is sized to mesh with portion 316 of pedicle screw 302, and an upper head 324. Head 324 is preferably spherical shaped, and contains a driving socket 326 within head 324. FIG. 18 shows screw system 300 in its assembled orientation, while FIG. 19 shows a top view of system 300, and FIG. 20 shows a cross-sectional view of FIG. 18.

Spherical shaped head 324 of inner screw 320 provides a smooth surface for the part of system 300 which would contact tissue with the patient's body, making it less likely for system 300 to cause irritation to the surrounding tissue. Head 324 also has a lower profile than any of the screw systems in use today, which also decreases the risk of tissue irritation for screw system 300, and FIG. 20 shows a cross-sectional view of FIG. 18.

Figure 21:
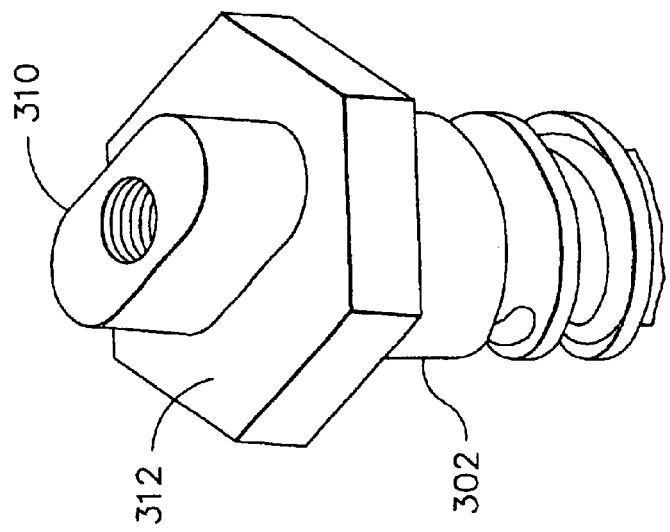
FIG. 21 is a fragmentary perspective view of the pedicle screw of the present invention.

Oval shaped extension 310 of pedicle screw 302 is shaped such that it may be accommodated nicely within slot 313 of plate 314 such that it prevents rotation of screw 302 when inner screw 320 is inserted, as can be seen in FIGS. 21 and 22. In the present embodiment, slot 313 measures approximately 6 mm, while the width of extension 310 is approximately 5 mm. In addition, the height of extension 310 is approximately 4 mm, while the thickness of plate 314 is approximately 5 mm, which allows inner screw 320 to firmly tighten plate 314 into position.

One problem that exists within all spinal plate systems is the risk of pedicle screw fracture when installing the inner screw. However, this risk decreases as the length of the inner screw increases. Pedicle screws rarely break in the anteriormost section. One cannot count on the inner screw to bottom out in the internal threads of the pedicle screw, as plates do not always sit flush against the spine. Often, washers are added to improve the plate/pedicle screw fit.

FIG. 23 shows a washer in use with the previously described plate system 300. Referring now to FIG. 23, a washer 330 is used to relieve stress caused by plate 314 not fitting flat against pedicle screw 302. Washer 330 consists of a flat lower surface 332, a raised edge 334 and an angled top surface 336. Washer 330 also has a rectangular opening 338 to accommodate extension 310 of pedicle screw 302. In operation, pedicle screw 302 is fixed into a vertebra by virtue of threaded section 304. Washer 330 is then installed by placing it onto pedicle screw 302 by inserting extension 310 through opening 338. Plate 314 is then placed over washer 330 and extension 310 such that extension 310 projects through opening 313 in plate 314. Inner screw 320 is finally inserted into the hollow threaded section 316 within pedicle screw 302 and tightened. Upper surface 336 of washer 330 sits flush against the bottom surface of plate 314. while lower surface 332 sits flush against surface 312 of screw 302.

Figure 25:
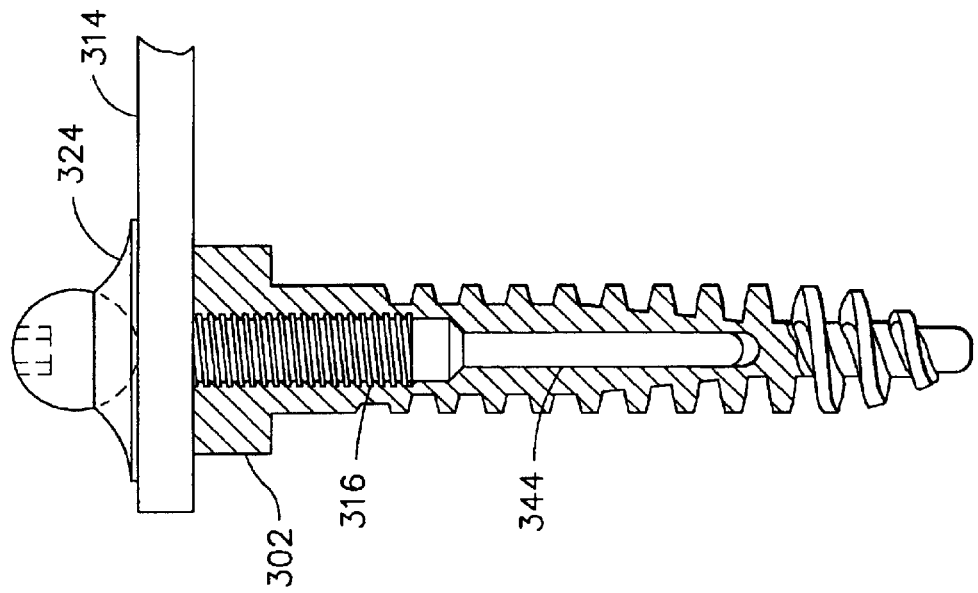
FIG. 25 is a fragmenting view, partly in cross section, of a plate system using the inner screw of FIG. 24.
Figure 24:
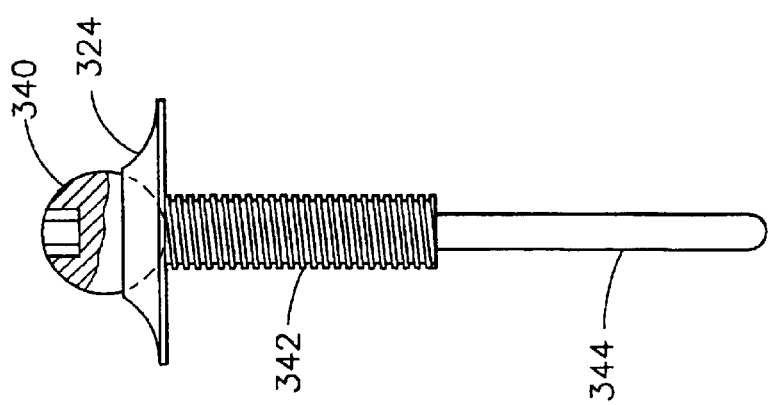
FIG. 24 is a die view of an inner screw according to the present invention.

Another device which may be helpful in reducing the stress which may affect the efficiency of the screw/plate system consists of a special inner screw, as can be seen in FIGS. 24 and 25. Referring now to FIG. 24, an inner screw 340 is shown having a lower threaded section 342 and head 324 as previously taught. At the end of section 342 there is a non-threaded aligning tip 344. As inner screw 340 is threaded into pedicle hollow section 316 and aids in the alignment of inner screw 340 as it enters section 316. Tip 344 extends into threaded section 316 of pedicle screw 302 almost to the bottom to assist in stress reduction within plate system 300, as can be seen in FIG. 25.

While the present invention has been shown and described in terms of preferred embodiments thereof, it will be understood that this invention is not limited to any particular embodiment, and that changes and modifications may be made without departing from the true spirit and scope of the invention as defined in the appended claims.

What is claimed is:

1. A system for rigidly coupling at least three vertebrae, which are not collinear, together on the spine, comprising:

an elongated plate having an upper and a lower surface, a first upper linear section, a second lower linear section, and a central curved section coupling said first and second sections, and having an opening located within the central region of said plate running along the central axis of said plate, with said central curved section and said lower linear section located at an angle with respect to said upper linear section;

a plurality of bone engaging screws each having a head for engaging said lower surface of said plate, an elongated shank with outer bone engaging threads, and an inner threaded hollow bore, wherein a bone engaging screw is affixed at each of the L4, L5 and S1 vertebrae;

and a plurality of inner screws each having a head and an elongated threaded shank;

wherein when said plate is positioned on the spine, a first inner screw is inserted through said curved section of said plate and fastened to the bone engaging screw at the L5 vertebra, a second inner screw is inserted through said first upper section of said plate and fastened to the bone engaging screw at the L4 vertebra, and a third inner screw is inserted through said second lower section of said plate and fastened to the bone engaging screw at the S1 vertebra, thus rigidly coupling these vertebrae together.

2. The system of claim 1, further comprising:

a bone engaging screw, affixed at the L3 vertebra;

and a fourth inner screw, wherein said fourth screw is inserted through said first upper section of said plate and fastened to the bone engaging screw at the L3 vertebra.

3. The system of claim 1, wherein said plate is manufactured from titanium.

4. The system of claim 1, wherein said angle is 10°.

5. The system of claim 1, further comprising a plurality of washers, each located between said head of said bone engaging screw and said lower surface of said plate.

6. The system of claim 5, wherein said washers each comprise a flat lower surface, a raised edge, a top surface angled in relation to said lower surface, and an opening in the central region of said washer.

7. The system of claim 1, wherein the head of said bone engaging screws is rounded.

8. A method of rigidly coupling the L4, L5 and S1 vertebrae of a spine together, comprising the steps of:

affixing a bone engaging screw having an elongated shank with outer bore engaging threads and an inner threaded hollow bore at the L4, L5 and S1 vertebrae;

positioning an elongated plate, having an upper surface and a lower surface and parallel side edges, an opening located within the central region of said plate running along the central axis of said plate, and having a first upper linear section, a second lower linear section, and a central curved section coupling said first and second sections, over said bone engaging screws, where said opening within said second linear section is located over the hollow bore of the screw at S1, said opening in said central curved section is located over the hollow bore of the screw at L5, and said opening within said first section is located over the hollow bore of the screw at L4;

and rigidly coupling said plate to the vertebrae by inserting an inner screw having a head and an elongated threaded shank into each bore engaging screw such that said plate is held firmly in the proper position between the head of the inner screw and said bore engaging screw.

9. The method of claim 8, wherein the coupling step further comprises placing a washer on each bone engaging screw which is captured between said bone engaging screw and the lower surface of said plate.

10. The method of claim 8, wherein the affixing step further includes affixing a bone engaging screw at the L3 vertebra, the positioning step includes positioning said plate such that said opening within said first linear section is located over the hollow bore of the bone engaging screw at L3.

11. A posterior lumbar plate system for rigidly coupling at least the L4, L5 and S1 vertebrae, which are not collinear, together on the spine, comprising:

an elongated plate having an upper and a lower surface, a first upper linear section, a second lower linear section, and a central curved section coupling said first and second sections, and having an opening located within the central region of said plate running within said first, central, and second sections along the central axis of said plate;

a plurality of bone engaging screws each having an upper surface for engaging said lower surface of said plate, and an elongated shank with outer bone engaging threads, wherein a bone engaging screw is affixed at each of the L4, L5 and S1 vertebrae;

and a plurality of fastening devices each having a surface for engaging said upper surface of said plate;

wherein when said plate is positioned on the spine, a first fastening device is fastened to the bone engaging screw at the L5 vertebra at said curved section of said plate, a second fastening device is fastened to the bone engaging screw at the L4 vertebra at said first upper section of said plate, and a third fastening device is fastened to the bone engaging screw at the S1 vertebra at said second lower section of said plate, thus rigidly coupling these vertebrae together.

12. The system of claim 11, further comprising:
a bone engaging screw, affixed at the L3 vertebra;
and a fourth fastening device,
wherein said fourth fastening device is fastened to the bone engaging screw at the L3 vertebra at said first upper section of said plate.

13. The system of claim 11, wherein said bone engaging screws each contain an inner threaded hollow bore.

14. The system of claim 13, wherein said fastening devices comprise a threaded shank and a head at one end of said shank shaped to receive a tool, such that said threaded shank may be affixed within said hollow bore of said bone engaging screws.

15. The system of claim 14, wherein said fastening devices further comprise nuts having an internally threaded opening such that said nuts may be affixed to said threaded shanks at a position contacting said plate.

16. The system of claim 11, wherein said upper surface of said bone engaging screws each contain a raised section which protrudes into said opening within said plate.

17. The system of claim 16, wherein said raised section is elongated in the longitudinal direction such that it is accommodated longitudinally within said opening within said plate.

18. The system of claim 11, wherein said bone engaging screws each contain a threaded extension extending through said plate and said fastening devices each contain an internally threaded opening capable of engagement with said threaded extensions of said bone engaging screws.

* * * * *